United States Patent
Kim et al.

(10) Patent No.: US 6,939,623 B2
(45) Date of Patent: Sep. 6, 2005

(54) HIGH STRENGTH STEEL PLATE HAVING SUPERIOR ELECTROMAGNETIC SHIELDING AND HOT-DIP GALVANIZING PROPERTIES

(75) Inventors: Eel-Young Kim, Pohang-si (KR); Jae-Young Lee, Pohang-si (KR); Jin-Gun Sohn, Pohang-si (KR); Noi-Ha Cho, Pohang-si (KR); Young-Jin Kwak, Pohang-si (KR); Soon-Joo Kwon, Pohang-si (KR); Yong-Min Kim, Pohang-si (KR); Jung-Sik Lee, Pohang-si (KR)

(73) Assignees: POSCO (KR); Research Institute of Industrial Science & Technology (KR)

(*) Notice: Subject to any disclaimer, the term of this patent is extended or adjusted under 35 U.S.C. 154(b) by 0 days.

(21) Appl. No.: 10/204,150

(22) PCT Filed: Dec. 19, 2001

(86) PCT No.: PCT/KR01/02213
§ 371 (c)(1),
(2), (4) Date: Aug. 16, 2002

(87) PCT Pub. No.: WO02/052914
PCT Pub. Date: Jul. 4, 2002

(65) Prior Publication Data
US 2003/0059643 A1 Mar. 27, 2003

(30) Foreign Application Priority Data
Dec. 19, 2000 (KR) .......... 2000-78772
Dec. 23, 2000 (KR) .......... 2000-81056

(51) Int. Cl.$^7$ .............................. B32B 15/04
(52) U.S. Cl. .................. 428/684; 428/686; 428/683; 428/659; 428/624; 428/626; 428/939; 148/320
(58) Field of Search ............... 428/684, 686, 428/683, 659, 470, 624, 626, 939; 148/318, 320, 306, 307; 174/35 MS

(56) References Cited

U.S. PATENT DOCUMENTS

| | | | |
|---|---|---|---|
| 5,019,191 A | | 5/1991 | Ogata et al. |
| 5,290,370 A | * | 3/1994 | Okada et al. .......... 148/330 |
| 5,542,994 A | * | 8/1996 | Seto et al. .......... 148/603 |
| 5,871,851 A | | 2/1999 | Fukumizu et al. |
| 6,025,673 A | | 2/2000 | Ikeda et al. |
| 6,282,848 B1 | | 9/2001 | Schlapfer |
| 6,432,228 B1 | * | 8/2002 | Uenishi et al. .......... 148/333 |
| 6,554,925 B2 | * | 4/2003 | Inoue et al. .......... 148/603 |

FOREIGN PATENT DOCUMENTS

| | | |
|---|---|---|
| EP | 0 508 479 A2 | 10/1992 |
| EP | 1 098 010 A1 | 5/2001 |
| EP | 1 114 880 A1 | 7/2001 |
| EP | 1 122 327 A | 8/2001 |
| JP | 54-115620 * | 9/1979 |
| JP | 62-185828 A | 11/1987 |
| JP | 01-032674 A | 2/1989 |
| JP | 07-032136 A | 2/1995 |
| JP | 08-098897 A | 4/1996 |
| JP | 10-096067 A | 4/1998 |
| JP | 10-208670 A | 8/1998 |
| JP | 6-17216 | 12/1998 |
| JP | 9-17216 * | 12/1998 |
| JP | 11-50207 A | 2/1999 |
| JP | 11-92886 A | 4/1999 |
| JP | 11-106876 A | 4/1999 |
| JP | 2000-008146 A | 1/2000 |
| JP | 2000-234152 A | 8/2000 |
| JP | 2001-107201 A | 4/2001 |
| JP | 2001-107202 A | 4/2001 |
| JP | 2001-217589 A | 8/2001 |
| KR | 1999-192767 B1 | 10/1995 |
| KR | 1996-005600 B1 | 4/1996 |
| KR | 1999-52018 A | 6/2001 |
| KR | 10-328078 B1 | 2/2002 |
| KR | 2000-80886 A | 6/2002 |
| KR | 2000-79907 A | 7/2002 |
| KR | 2000-81056 A | 7/2002 |
| WO | WO 96/10901 A1 | 4/1996 |
| WO | WO 97/11204 A1 | 7/1998 |
| WO | WO 00/34411 A1 | 6/2000 |

* cited by examiner

Primary Examiner—Jennifer McNeil
(74) Attorney, Agent, or Firm—Webb Ziesenheim Logsdon Orkin & Hanson, P.C.

(57) ABSTRACT

The steel plate is manufactured from a composition comprising C, N and S in an amount of 0.0150% by weight or less in total; Mn in an amount of 0.2 to 0.8% by weight; Al in an amount of 0.6% by weight or less; Si in an amount of 0.4% by weight or less; Cu and/or Sn in an amount of 0.1 to 0.6% by weight in total; and Fe for the remainder, and inevitably present elements, whereby the steel plate can show excellent electromagnetic shield effect and hot-dip galvanization properties.

4 Claims, No Drawings

HIGH STRENGTH STEEL PLATE HAVING SUPERIOR ELECTROMAGNETIC SHIELDING AND HOT-DIP GALVANIZING PROPERTIES

BACKGROUND OF THE INVENTION

1. Field of the Invention

The present invention relates to a high-strength steel plate with excellent electromagnetic shield and hot-dip galvanization properties, which is suitable for use where high corrosion resistance is required, like construction finishes. More particularly, the present invention relates to a high-strength steel plate with excellent electromagnetic shield and hot-dip galvanization properties, which shows a shield effect of 25 dB (shield efficiency 93%) or higher against electromagnetic fields at 60 Hz and a yield strength of 22 kg/mm² or higher.

2. Description of the Prior Art

Many natural and human-made sources generate electromagnetic energy in the form of electromagnetic waves. These waves consist of oscillating electric and magnetic fields which interact differently with biological systems such as cells, plants, animals, or human beings. The finding of electromagnetic waves having detrimental effects on the body has led to the development of various methods and materials for shielding electromagnetic waves. Waves adversely affecting the body are collectively called harmful waves.

Recent studies have demonstrated harmful effects of electromagnetic waves at low frequencies on biological systems. Particularly, a series of studies results revealing the interrelation of the electromagnetic field (60 Hz) around power transmission lines with carcinogenesis has had great repercussions all over the world.

In addition to carcinogenic effects, low frequency waves with magnetic properties are found to cause inductive currents in the body upon exposure to the waves for a long period of time, upsetting the biological balance of various ions, such as $Na^+$, $K^+$, $Cl_-$ and so forth, across cellular membranes, which results in adversely affecting the hormone secretion and immunocytes of the body.

Further, other studies showed the influence of magnetic fields on the secretion of melatonin, a hormone responsible for regulating the sleep cycle, adding that the body may suffer from insomnia upon prolonged exposure to magnetic fields.

In order to cope with such harmful electromagnetic waves, shielding technology has been developed in two aspects: structure and material. With regard to the construction aspect, magnetically shielded rooms are disclosed in U.S. Pat. No. 6,282,848 and Japanese Pat. Laid-Open Publication No. Hei. 7-32136. Electrically conductive materials such as copper are in current use as shields against electromagnetic waves, as disclosed in Japanese Pat. Laid-Open Publication No. 2001-217589. However, such materials are useful only for electromagnetic waves at high frequencies (1 KHz or higher).

Electromagnetic waves at 60 Hz, usually detected in general power sources, are composed of an electric field and a magnetic field component, which both vary with time. Accordingly, in order to shield these low frequency electromagnetic waves, which have recently been shown to have adverse health effects, time-varying electric and magnetic fields should be considered together. However, there have not yet been developed practical technologies for steel plates that can effectively shield time-varying electromagnetic fields.

Conventionally, steel plates with high magnetic permeability are used as magnetic shields. For instance, Japanese Pat. Laid-Open Publication Nos. Hei. 10-208670 and Hei. 10-96067 and PCT WO 97/11204 disclose static magnetic field-shielding steel plates which can be adopted in color image tubes of, for example, TV monitors, with the aim of preventing color modulation on the monitors. Such steel plates are used to take advantage of their coercive force and permeability under static magnetic fields such as earth magnetic field, but cannot cope with time-varying magnetic and electric fields. Accordingly, the conventional steel plates are somewhat different from electromagnetic wave shields.

As occasion demands, construction materials are required to not permit the permeation of electromagnetic waves thereto. In this regard, hot-rolled thick plates using silicon steel are suggested for use in electromagnetic field shield constructions, as disclosed in Japanese Pat. Laid-Open Publication Nos. 2001-107201 and 2001-107202. The construction materials, however, take advantage only of the high permeability of silicon steel under static magnetic fields, and are not described in terms of electric fields. Further, the steel plates are poor in mechanical formability and platability (the property of galvanized coating) because they are not cold-rolled but hot-rolled.

Also, the present inventors disclosed a steel material with excellent magnetic shield effect at low frequencies in Korean Pat. Appl'n No. 1999-52018. The shield effect is a theoretical value obtained from the permeability and conductivity measured under static magnetic fields, and thus differs from real values, finding difficulty in practical application. Thus, there remained a need for shield evaluation under time-varying magnetic fields.

Meeting this need, methods for evaluating the magnetic shielding effect of steel plates according to frequencies were developed (Korean Pat. Nos. 2000-79907 and 2000-80886), and are in current use.

Typically, the shielding efficiency of a steel plate can be obtained by the following equations:

$$\text{Magnetic Shield Efficiency} = \frac{\text{Applied Magnetic Field} - \text{Transmitted Magnetic Field}}{\text{Applied Magnetic Field}} \times 100 \quad \text{Equation 1}$$

$$\text{Electric Shield Efficiency} = \frac{\text{Applied Electric Field} - \text{Transmitted Electric Field}}{\text{Applied Electric Field}} \times 100 \quad \text{Equation 2}$$

Expressed as dB units, the shield effect of a steel plate can be obtained by the following equations:

$$\text{Magnetic Shield Effect} = -20 \log \frac{\text{Transmitted Magnetic Field}}{\text{Applied Magnetic Field}} \quad \text{Equation 3}$$

$$\text{Electric Shield Effect} = -20 \log \frac{\text{Transmitted Electric Field}}{\text{Applied Electric Field}} \quad \text{Equation 4}$$

According to the equations, the shield effect of a shielding material having a shielding efficiency of 90% (attenuation of electromagnetic waves to one tenth) can be expressed as 20 dB. A shielding efficiency of 95% (attenuation of electromagnetic waves to one twentieth) corresponds to a shield effect of about 26 dB.

Korean Pat. Appl'n No. 2000-81056 to the present inventors is directed to a biowave steel plate based on an electromagnetic shielding cold-rolled steel plate on which powders emitting far-infrared radiation are coated. To improve the shielding effect against time-varying magnetic fields, that is, to obtain high permeability under time-varying magnetic fields, the biowave steel plate for shielding electromagnetic waves contains carbon in an amount of 0.02% or less and Si in an amount of 0.5–3.5%.

As for cold-rolled steel plates with a carbon content less than 0.02%, they are unsuitable for use in construction owing to their poor strength. Lower carbon contents in the steel plate make the grains of the steel microstructure coarser, improving the magnetic shield effect, but lowering the strength. Therefore, cold-rolled steel plates with low carbon contents are not suitable for use where high strength is required.

Also, the silicon steel plates are too high in strength and very poor in mechanical formability (elongation 40% or less), so that they are very difficult to apply to construction and household appliances which require mechanical formability of materials.

For use in exterior environments, like construction exterior finishes, silicon steel plates must be corrosion-resistant. In this regard, hot-dip galvanizing with anti-corrosive materials is carried out on such exterior finishes. However, the presence of Si is apt to cause plating defects, such as uncoating, upon the hot-dip galvanization of the steel plate. In fact, electromagnetic shield steel plates applied to highly corrosive environments, like construction finishes, are required to be hot-dip galvanized with zinc at a coating density of at least 100 g/mm$^2$.

SUMMARY OF THE INVENTION

Therefore, it is an object of the present invention to overcome the above mentioned problems encountered in the prior art and to provide a high-strength steel plate and a hot-dip galvanized steel plate, which show a yield strength of 22 kg/mm$^2$ or higher and a shield effect of 25 dB (shield efficiency 93%) or higher against time-varying electromagnetic fields at 60 Hz on the basis of 1 mm thickness of the plate.

It is another object of the present invention to provide a method for manufacturing such a steel plate.

In an aspect of the present invention, there is provided a high-strength steel plate, prepared from a composition comprising C, N and S in an amount of 0.0150% by weight or less in total; Mn in an amount of 0.2 to 0.8% by weight; Al in an amount of 0.6% by weight or less; Si in an amount of 0.4% by weight or less; Cu and/or Sn in an amount of 0.1 to 0.6% by weight in total; and Fe for the remainder, and inevitably present elements, whereby the steel plate can show excellent electromagnetic shield capacity and hot-dip galvanization property.

In another aspect of the present invention, there is provided a method for manufacturing a high-strength steel plate, comprising the steps of: providing a steel slab comprising C, N and S in an amount of 0.0150% by weight or less in total; Mn in an amount of 0.2 to 0.8% by weight; Al in an amount of 0.6% by weight or less; Si in an amount of 0.4% by weight or less; Cu and/or Sn in an amount of 0.1 to 0.6% by weight in total; and Fe for the remainder, and inevitably present elements; reheating the steel slab at 1,110 to 1,290° C.; hot-rolling the steel slab at a final deformation temperature of 900° C. or higher to give a hot-rolled steel plate, followed by coiling the hot-rolled steel plate; cold-rolling the steel plate at a reduction percentage of 50–70% and annealing, whereby the steel plate can be improved in electromagnetic shield effect and hot-dip galvanization property.

In a further aspect of the present invention, there is provided a method for manufacturing a high-strength hot dip galvanized steel plate, comprising the steps of: providing a steel slab comprising C, N and S in an amount of 0.0150% by weight or less in total; Mn in an amount of 0.2 to 0.8% by weight; Al in an amount of 0.6% by weight or less; Si in an amount of 0.4% by weight or less; Cu and/or Sn in an amount of 0.1 to 0.6% by weight in total; and Fe for the remainder, and inevitably present elements; reheating the steel slab at 1,110 to 1,290° C., hot-rolling the steel slab at a final deformation temperature of 900° C. or higher to give a steel plate to give a hot-rolled steel plate, followed by coiling the hot-rolled steel plate; cold-rolling the steel plate at a reduction percentage of 44~70% and annealing; and hot-dip galvanizing the steel plate and optionally subjecting the steel plate to skin pass at a reduction percentage 0.2–1.0%, whereby the steel plate can be improved in electromagnetic shield effect and hot-dip galvanization property.

DETAILED DESCRIPTION OF THE INVENTION

Magnetic fields are generated by currents, while electric fields are induced by voltages. At low frequencies, electromagnetic waves are separated into electric and magnetic components. To be used as an electromagnetic shield, a material must attenuate or shield both of the electric and magnetic components.

The magnetic shield effect of a material against magnetic fields at low frequencies is determined by the ability to alter magnetic flux paths and to cause eddy current loss. Herein, the alteration of a magnetic flux path means that, when a harmful magnetic field is incident upon a shield material, a path through which the magnetic field can flow is generated on the surface of the material, so that the magnetic field is not led to an interior of the shield material, but guided elsewhere to dissipate. Herein, the eddy current loss indicates that, when being incident upon a shield material, a magnetic field in wave form is dissipated as heat energy at the surface of the shield material by an eddy current which circulates on the material in the direction of eliminating the magnetic field. Materials with higher permeability are more advantageous in the alteration of magnetic flux paths. Also, the eddy current loss generated at low frequencies is typically increased with increasing of the electric conductivity and magnetic permeability of a shield material. Hence, steel plates with high permeability and electric conductivity at 60 Hz exhibit excellent low-frequency magnetic field shielding properties.

Electric fields can be induced upon generation of potential differences even if currents do not flow. To prevent the induction of an electric field in a shielded space, it must be in an equipotential state. Desirable as electric shields are materials with high volume electric conductivity because higher electric conductivity is more advantageous in preventing the generation of a potential difference.

In the experience of the present inventors, it was very difficult to exactly measure the conductivity and permeability of a material in the presence of a time-varying electric field, such as electromagnetic waves. In addition, the preparation of samples was so complex as to cause large errors in the measurement of the conductivity and permeability.

In the present invention, steel plates are measured for shield capacity against magnetic and electric fields. In this regard, low-frequency magnetic shield capacity was evaluated by use of an apparatus for measuring magnetic shield capacity under time-varying magnetic fields (Korean Pat. Nos. 2000-79907 and 2000-80886). As for shield capacity against time-varying electric fields, it is determined by the ratio of electric field intensities measured in a shielded room in the presence of and in the absence of a shielding material using a voltage source of 1,200 volts/m at 60 Hz, positioned outside of the shielded room.

The present invention pertains to high strength steel plate shields against electric and magnetic fields.

Steel plates may comprise various elements in addition to Fe. The alloy elements that are generally added to ferromagnetic Fe to improve the strength and corrosive resistance of steel plates affect the maximal permeability and electric conductivity under time-varying magnetic fields (60 Hz). Also, the permeability and electric conductivity varies with the carbon content and grain size of the steel plate. Of course, steel plates show different mechanical properties according to composition due to the change of strengthening mechanisms such as solid-solution hardening, grain size refinement, etc.

In accordance with the present invention, there is provided a steel plate which has a strength suitable for use in construction and furniture panels, that is, a yield strength of 22 kg/mm$^2$ or higher, as well as an electromagnetic shield capacity of 93% (25 dB) or higher. Through the thorough and intensive experiments conducted by the present inventors, in which steel plates were measured for electromagnetic shield effect and mechanical strength while being changed in composition, the role of each component in determining the electromagnetic shield effect and strength of the steel plate are defined. Particularly, C, N, S, Si, Mn, Al, Cu and Sn were found to have great influence on the shield capacity and strength of the steel plate. Based on the results of the experiments, an optimal steel composition system could be obtained. Additional experiments resulted in the finding that contents of additive elements, such as Si, Mn, Al, Cu and Sn, are related to the hot-dip galvanization of the steel plate, leading to a steel composition superior in hot-dip platability as well as shield capacity and strength.

On the whole, the electromagnetic shield effect of a steel plate is largely dependent on its content of interstitial elements such as N, C and S, or elements which can form the precipitate. For instance, the internal strain of steel increases with increasing of the content of C, N and S and increase the strength due to strain-hardening. Also, the interstitial elements C, N and S are precipitated as forms of $Fe_3C$, AlN and MnS, respectively, thereby increasing the strength of the steel.

However, the increased strain and formed precipitates give rise to a great decrease in the permeability and electric conductivity of the steel, thus deteriorating shield properties of the steel. In fact, it is very difficult to provide steel with an appropriate strength as well as a shield efficiency of 95% (25 dB) or higher by use of such interstitial elements only.

In accordance with the present invention, the sum of C, N and S, which have a fatal influence on electromagnetic shield properties of steel plates, is limited to up to 0.015% by weight in the composition of the steel.

Preferably, C and N are each contained in an amount of 0.0030% or less, while the content of S is controlled to an amount of 0.0090%, so as to ensure the steel being of electromagnetic shield effect and mechanical formability.

Where the interstitial elements C, N and S are used in the above-defined amounts, the steel becomes poor in strength. In order to compensate for the weak strength attributed to the minimal contents of the interstitial elements, other elements are needed to induce such solid-solution hardening as to increase the strength of the steel. However, restrictions must be imposed on the amount and kind of elements used to improve strength, lest they deteriorate the electromagnetic shield effect by inducing too large a decrease in permeability and electric conductivity. Particularly, the amount and kind of the additive elements are restricted by the hot-dip galvanization properties of the steel plates because the properties are greatly affected by the additive elements.

Mn is contained in the steel plate of the present invention. The electric shield capacity of the steel plate does not vary with Mn content, because the element does not affect the electric conductivity of the steel plate. However, the mechanical properties and magnetic shield effect of the steel plate are greatly affected by the Mn content.

To an amount of 0.2% by weight, Mn generally makes contribution to the magnetic shield effect and elongation of the steel plate, in addition to guaranteeing an appropriate strength. However, plating defects may occur upon hot-dip galvanization in the presence of 0.8% by weight or higher of Mn. Considering these effects, Mn is used in an amount of 0.2 to 0.8% by weight.

Si is also contained in the steel plate of the present invention. Increasing the content of Si may increase the strength of the steel, but may decrease the magnetic shield effect.

In the present invention, the content of Si is limited to up to 0.4% by weight. If present in too large an amount, Si, which is readily oxidized, forms $SiO_2$ on the surface of the cold-rolled steel plate and the oxide adversely affects the platability.

The steel plate of the present invention may comprise Al. Al improves the strength of the steel and slightly decreases the electric shield effect without a significant reduction in shield effect against magnetic fields. Al is contained in an amount of up to 0.6% by weight in accordance with the present invention. More than 0.6% by weight of Al gives rise to a great decrease in the platability.

In electromagnetic shield effect, mechanical properties and hot-dip galvanization, Al shows behaviors similar to those of Si. It is believed that the similar behaviors are attributed not only to the similarity between the two elements in terms of their influence on the permeability and conductivity of the steel plate and in the strengthening mechanism, but also to the fact that both the two elements are readily oxidized to form oxides on the surface of the steel plate, adversely affecting the platability.

In accordance with the present invention, Cu and Sn are contained in steel plates. Cu and Sn were found to bring about an improvement in electromagnetic shield effect with concurrent increase of strength. Also, it was found that neither Cu nor Sn adversely affects the hot-dip galvanization of the steel plate because they are not readily oxidized unlike Si and Al.

The strength-improving mechanism of Cu and Sn can be explained by the hardening effect due to the solid-solution of Cu and Sn. As a rule, when solid-solution hardening occurs in a steel alloy, its internal strain reduces the permeability, or grains become fine, decreasing the permeability and conductivity. In spite of the solid-solution hardening resulting from the addition of Cu and/or Sn, the steel plate is not significantly lowered in permeability and conductivity. It is believed that the addition of the elements develops the texture of the magnetic easy axis <100> with almost no change in the size of crystal grains.

Without significantly reducing the magnetic shield, Cu and Sn can improve the strength of the steel plate, and may be used individually or in combination in the present invention.

Preferably, the sum of Cu and Sn is limited within the range of 0.1~0.6% by weight. For example, at less than 0.1%, Cu and Sn do not exhibit their effects, nor guarantee the desired strength (yield strength 22 kg/mm$^2$ or higher). On the other hand, when Cu and Sn is used in an amount more than 0.6% in total, not only is the magnetic shield effect decreased, but also the hot-dip galvanization is not successfully performed on the steel plate.

It is advantageous in terms of electromagnetic shield and strength that Cu and Sn are used in combination with Si, Al and Mn. In the present invention, the sum of Cu, Sn, Al, Mn and Si is limited to 1% by weight or less.

Also, the present invention pertains to a method for manufacturing steel plates and hot-dip galvanized steel plates.

First, a steel slab prepared from the composition defined above is reheated. In this regard, the slab reheating temperature (SRT) is limited within the range of 1,110~1,290° C.

When the SRT is below 1,110° C., so insufficient in the course of continuous processes is the descaling time that scale defects may be generated. Or, such a low temperature as is less than 1,110° C. causes hot rolling to be conducted in a two-phase region (ferrite+austenite region), thereby problems such as material property variation occurring in the slab. On the other hand, an SRT higher than 1,290° C. requires a large expense for energy and facilities. In addition, the oxide coat formed on the surface of the slab at an SRT of 1,290° C. is too thick to descale the slab, resulting in surface defects.

Within the SRT range, (Mn, Cu, Sn)S precipitates increase in size with increasing of the temperature, thereby effectively improving the electromagnetic shield capacity. However, when the temperature exceeds 1,200° C., the re-melted (Mn, Cu, Sn)S in the slab is re-precipitated and dispersed finely to make the grain size of the slab small. The reduction in grain size due to fine precipitate inhibits the growth of grains in the annealing procedure of the subsequent cold-rolling process, bringing about a slight reduction in the shield effect.

Therefore, the SRT preferably falls within the range of 1,110 to 1,200° C.

Next, the re-heated slab is hot-rolled with a final deforming temperature (FDT) being 900° C. or higher. When the FDT is below 900° C., the two-phase region (ferrite+austenite region) is subjected to rolling, which causes material property variation, and surface defects such as orange peel. For these reasons, the FDT is limited to 900° C. or less.

Afterwards, the hot-rolled steel plate is coiled. Preferably, the coiling temperature (CT) is restricted within the range of 610 to 750° C. because the grain size in cold-rolled products is greatly affected by the grain size of the hot-rolled steel plate after hot-rolling. In detail, At a CT lower than 610° C., the grains do not grow sufficiently. On the other hand, a CT higher than 750° C. may not allow grains to grow further.

Subsequently, the coiled, hot-rolled steel plate was pickled with acid, followed by cold rolling and annealing.

Generally, the electromagnetic shield effect of a steel plate is greatly dependent on its grain size. A steel plate with large grain sizes allows magnetic domains to freely move within grains, thereby improving the magnetic shield capacity. Accordingly, it is important to control cold-rolling process conditions because the process may alter the grain size and thus have great influence on the electromagnetic shield effect.

As reduction percentages during cold rolling are lower, the hot-rolled texture after the cold rolling is hardly broken. Accordingly, nucleation sites in which recrystallization occurs upon annealing are reduced in number, so that grain sizes after annealing may be increased. However, low reduction percentages during continuous cold rolling make it difficult to control the shape of the steel plate. Besides, the production efficiency is lowered at reduction percentages.

On the other hand, at too high reduction percentages, the crystal grains of the cold-rolled steel plate become so fine as to deteriorate the electromagnetic shield effect of the steel plate.

For these reasons, the reduction percentage for the cold rolling is defined within the range of 50 to 70% in the present invention.

Thereafter, the cold-rolled steel plate is annealed under typical conditions to give high-strength cold-rolled steel plate which has a yield strength of 22 kg/mm or higher and a shield efficiency of 93% (25 dB) or higher under a time-varying electromagnetic field at 60 Hz, in addition to being superior in hot-dip galvanization property.

In order to provide corrosion resistance to the steel plate comprising the above-defined composition, it may be hot-dip galvanized with an anti-corrosive element such as zinc or aluminum. After hot-dip galvanization, the steel plate may be subjected to skin pass in order to control shape and roughness of steel pate.

Skin pass, however, lowers the permeability under time-varying magnetic fields, thereby deteriorating the magnetic shield effect of the steel plate. However, defects such as plate distortion cannot be controlled without skin pass. Therefore, it is preferred that skin pass is conducted as little as possible.

To avoid such defects as plate distortion, at least 0.2% elongation is required. On the other hand, when the reduction percentage exceeds 1.0%, a drastic internal strain is introduced into the steel plate which is thus greatly lowered in electromagnetic shield effect. Therefore, skin pass is preferably conducted at a reduction percentage of 0.2 to 1.0% in the present invention.

Such skin pass can effectively detour around the plate distortion attributed to a cold-rolling reduction percentage of as low as 44–50%. Thus, when the skin pass is conducted, the cold rolling reduction percentage can be extended from 50% to 44%. In other words, the skin pass can be omitted in the present invention because plate distortion does not occur in the cold rolling reduction percentage range of 50~70%.

The high-strength steel plate of the composition, as mentioned above, can be improved in corrosion resistance by hot-dip galvanization with zinc or aluminum.

Compared to uncoated cold-rolled steel plates, the hot-dip galvanized steel plates are slightly increased in electromagnetic shield capacity, but decreased in yield strength. This is because the cold-rolled steel plates are thickened as zinc, which is of higher conductivity and lower strength than iron, is coated on the plates. However, there is no detectable difference in electromagnetic shield and strength between the hot-dip galvanized steel plates and bare plates.

Plating methods do not limit the application of the steel plates of the present invention. Since hot-dip galvanized steel plates can be generally fabricated by electroplating, the steel plates of the present invention can be coated with anti-corrosive elements such as zinc and aluminum in an electroplating manner.

In accordance with the present invention, the steel plate may be coated with an organic resin layer so as to express a color on the steel plate. After being coated with a pigment-containing organic resin such as polyethylene, the steel plate, so-called pre-coated metal, maintains the characteristic electromagnetic shield effect and mechanical properties that it has before, not only because the pigment contained in the resin is non-magnetic but also because the coating is as thin as 25 $\mu$m.

In accordance with the present invention, far-infrared radiation emitting powder with a radiation efficiency (emissivity) of 0.9 or higher may be formed to a thickness of 15 to 60 $\mu$m on the coating layer of the steel plate. Preferably, the far-infrared radiation emitting powder has a specific surface area of 1 $m^2/g$ or higher and comprises 17–99% of $Mg(OH)_2$.

annealing simulator, annealing was carried out at 850° C. to produce cold-rolled steel plates. Zinc was coated on each cold-rolled steel plate at a coating density of 300 $g/m^2$ by use of a hot dip galvanizing simulator.

With the aid of an electromagnetic shield effect analyzer, each of the hot dip galvanized steel plates was measured for electromagnetic shield effect at 60 Hz, and the results are given in Table 1, below. Also, the mechanical properties, such as yield strength and elongation, of the steel plates, were measured by use of a universal testing machine and summarized in Table 1, below.

Determined through observation with the naked eye and testing for coat adhesion, the platability of the hot-dip galvanized steel plates was expressed as O for a good state and as X for the presence of fatal plating defects, in Table 1.

TABLE 1

| Composition No. | Component (Wt %) | | | | | | Magnetic Shield (dB) | Electric Shield (dB) | Yield Strength ($Kg/mm^2$) | Hot-dip Galvanization Property |
|---|---|---|---|---|---|---|---|---|---|---|
| | Si | Al | Mn | P | Cu | Sn | | | | |
| Compar. 1 | Tr. | Tr. | Tr. | Tr. | Tr. | Tr. | 28.2 | 41.5 | 14.2 | O |
| Compar. 2 | 0.6 | Tr. | 0.2 | Tr. | Tr. | Tr. | 25.5 | 38.2 | 27.4 | X |
| Compar. 3 | 0.8 | Tr | 0.2 | Tr. | Tr. | Tr. | 22.8 | 38.0 | 28.6 | X |
| Compar. 4 | 0.3 | 0.6 | 0.2 | Tr | Tr. | Tr. | 21.6 | 37.7 | 26.3 | X |
| Compar. 5 | Tr | Tr | 0.2 | Tr. | Tr. | Tr. | 28.2 | 40.7 | 18.0 | O |
| Compar. 6 | 0.2 | Tr | 0.2 | Tr. | Tr. | Tr. | 28.1 | 40.5 | 22.0 | O |
| Compar. 7 | Tr. | 0.2 | 0.2 | Tr. | Tr. | Tr. | 26.9 | 40.5 | 20.6 | O |
| 1 | Tr | Tr | 0.2 | Tr. | 0.1 | 0.1 | 27.8 | 40.8 | 22.3 | O |
| 2 | Tr. | 0.2 | 0.2 | Tr. | 0.3 | 0.3 | 25.4 | 40.1 | 25.7 | O |
| 3 | 0.2 | Tr | 0.2 | Tr. | 0.2 | 0.2 | 27.6 | 40.2 | 25.4 | O |
| 4 | 0.2 | Tr | 0.2 | Tr. | Tr. | 0.5 | 25.4 | 40.3 | 26.3 | O |
| 5 | 0.2 | Tr | 0.2 | Tr. | 0.5 | Tr. | 25.1 | 40.1 | 26.7 | O |
| Compar. 8 | Tr. | Tr | 0.2 | Tr. | 0.03 | 0.02 | 27.3 | 40.8 | 18.8 | O |
| Compar. 9 | 0.2 | Tr | 0.2 | Tr. | 0.4 | 0.4 | 21.8 | 39.5 | 27.9 | X |

Having generally described this invention, a further understanding can be obtained by reference to certain specific examples which are provided herein for purposes of illustration only and are not intended to be limiting unless otherwise specified.

EXAMPLE 1

Steel compositions were prepared with different Cu, Sn contents and the like as shown in Table 1, below, and 30 kg of each steel composition was vacuum melted. In Table 1, the expression "Tr" means no addition of the element. In each composition, C and N were each contained in an amount of 0.0030% or less, while the content of S was controlled in an amount of 0.0090%.

The melted compositions were re-heated at 1,250° C., and hot-rolled with the final deforming temperature being maintained at 900 C., to give hot-rolled steel plates each 2 mm thick. Hot-rolled scales were removed from the steel plates by pickling with acid. The acid-pickled, hot-rolled steel plates were cold-rolled to a thickness of 1 mm at a reduction percentage of 50%. Subsequently, using a consecutive As apparent from the data of Table 1, the steel plates of the present invention (Composition Nos. 1 and 2), each of which maintained Cu, Sn and Si within the range defined according to the present invention, showed excellent strength without sacrifice of electromagnetic shield effect. Additionally, the steel plates were found to be excellent in platability.

In contrast, Comparative Composition No. 1, which contained none of Cu, Sn, and Si, although superior in shield effect, was too low in strength to be suitable for use in the present invention. Where the Si content was over 0.4% (Comparative Composition Nos. 2 and 3), platability was poor and plating defects were observed due to uncoated regions.

Comparative Composition Nos. 4 to 7 which contained Mn and/or Si, but neither Cu nor Sn showed strength only in the range 18 to 22 $kg/mm^2$ which does not reach the required strength, 22 $kg/mm^2$ or higher. In addition, some of them showed high strength (>22 $kg/mm^2$), but could not be hot-dip galvanized. Particularly, when the sum of Si, Al and Mn exceeded 1.0% (Comparative Composition No. 4), a decrease in electromagnetic shield effect was observed and particularly, the hot-dip galvanizing property was greatly deteriorated.

When the sum of Cu and Sn was below 0.1% (Comparative Composition No. 8), the shield effect and the hot-dip galvanization property were excellent, but the strength was low. On the other hand, when the sum of Cu and Sn was over 0.6% (Comparative Composition No. 9), the strength was very high, but drastic decreases were found in magnetic shield effect and hot-dip galvanization property.

EXAMPLE 2

30 kg of a composition comprising C in an amount of 0.003% or less, N in an amount of 0.003% or less, Mn in an amount of 0.2%, Al in an amount of 0.2%, Si in an amount of 0.2%, Cu in an amount of 0.2% and Sn in an amount of 0.2% was vacuum melted. The melted slabs were prepared into hot-rolled steel plates, each 2mm thick, under various temperature conditions, including reheating temperature, final deforming temperature, and coiling temperature. The steel plates were pickled with acid to remove hot-rolled scales therefrom. The acid-pickled hot-rolled steel plates were cold-rolled to a thickness of 1mm at a reduction percentage of 50%. Subsequently, using a consecutive annealing simulator, annealing was carried out at 850° C. to produce cold-rolled steel plates.

With the aid of an electromagnetic shield effect analyzer, each of the cold-rolled steel plates was measured for electromagnetic shield effect at 60 Hz, and the results are given in Table 2, below. Also, the mechanical properties, such as yield strength, of the steel plates, were measured by use of a universal testing machine and summarized in Table 2, below. With the naked eye, the cold-rolled steel plates were observed to determine the presence of scales on their surfaces.

TABLE 2

| Steel No. | Hot Rolling (° C.) SRT | FDT | CT | Magnetic Shield (dB) | Electric Shield (dB) | Yield Strength (Kg/mm$^2$) | Surface Condition |
|---|---|---|---|---|---|---|---|
| 1 | 1250 | 910 | 700 | 25.3 | 40.5 | 25.9 | Excellent |
| 2 | 1200 | 910 | 700 | 25.4 | 40.5 | 25.7 | Excellent |
| 3 | 1150 | 910 | 700 | 26.5 | 41.0 | 25.3 | Excellent |
| Compar. 1 | 1100 | 910 | 700 | 27.2 | 41.1 | 27.1 | Poor |
| Compar. 2 | 1150 | 895 | 700 | 29.2 | 41.2 | 25.8 | Poor |
| Compar. 3 | 1150 | 870 | 700 | 24.7 | 40.5 | 26.6 | Poor |
| 4 | 1150 | 900 | 700 | 26.4 | 40.8 | 25.3 | Excellent |
| 3 | 1150 | 900 | 750 | 26.5 | 41.1 | 25.8 | Excellent |
| 5 | 1150 | 900 | 650 | 26.2 | 41.0 | 25.9 | Excellent |
| Compar. 4 | 1150 | 900 | 600 | 24.5 | 41.0 | 25.9 | Excellent |

As seen in Table 2, steel plates of the present invention (Steel Nos. 1 to 5), which were all prepared under suitably controlled reheating and coiling temperatures, all were found to be superior in electromagnetic shield properties and be descaled so completely as to form no hot-rolled plating defects.

Particularly, the electromagnetic shield effect was greatly increased when the slab reheating temperatures (SRT) were in the range defined in the present invention. The improvement in electromagnetic shield effect was believed to be attributed to the fact that (Mn, Cu, Sn) S, aggregates of the components Mn, Cu and Sn and the impurity S, are not newly precipitated, so that (Mn, Cu, Sn)S precipitates and grain sizes remain coarse.

In the case of Steel Nos. 1 and 2 in which the SRT was over 1,200° C., descaling was conducted sufficiently to prevent surface defects, but new precipitation of (Mn, Cu, Sn)S occurred during a cooling procedure after the reheating, making the grain size small. For these reasons, the steel plate of Steel Nos. 1 and 2 were of lower electromagnetic shield effect than those of Steel Nos. 3 to 5. Therefore, the SRT is preferably limited within the range of 1,110 to 1,200° C.

By contrast, at an SRT less than 1,110° C. (Comparative Steel No. 1), it was difficult to secure a sufficient descaling time. Therefore, on the surface of the cold-rolled steel plates were formed defects which were subsequently remained onto the surface of the steel plate upon hot-dip galvanization.

At FDT below 900° C., two-phase regions (ferrite +austenite regions) were rolled to generate material variation and plate distortion, along with numerous surface defects.(comparative No. 2 and 3)

Also, a drastic decrease was found in electromagnetic shield effect at a coiling temperature less than 600° C. (Comparative Steel No. 4) as grains became small.

It is apparent in Table 2 that high coiling temperatures tend to increase electromagnetic shield capacity, but decrease strength. This is because grains grow at high temperatures to bring about an improvement in permeability and conductivity under time-varying electromagnetic fields.

EXAMPLE 3

30 kg of a composition comprising C in an amount of 0.003% or less, N in an amount of 0.003% or less, S in an amount of 0.008%, Mn in an amount of 0.2%, Al in an amount of 0.2%, Si in an amount of 0.2%, Cu in an amount of 0.2% and Sn in an amount of 0.2% was vacuum melted.

After being reheated at 1,200° C., the melted composition was prepared into hot-rolled steel plates with thickness of 1.8, 2.0, 3.0 and 4.0 mm, while FDT and CT were set at 910 and 680° C., respectively. Then, steel plates were cold-rolled to a thickness of 1 mm at different reduction percentages as shown in Table 3. Annealing was done at 850° C., followed by hot-dip galvanizing the plates with zinc to a coating density of 180 g/m$^2$. Some of the resulting hot-dip galvanized steel plates were subjected to skin pass at different reduction percentages.

With the aid of an electromagnetic shield effect analyzer, a measurement was made of electromagnetic shield effect at 60 Hz of each of the cold-rolled steel plates, and the results are given in Table 3, below. Also, the mechanical properties (yield strength) of the steel plates, were measured by use of a universal testing machine and summarized in Table 3, below. With the naked eye, the cold-rolled steel plates were observed to determine the presence of shape defect of steel plate(plate distortion).

TABLE 3

| Steel No. | Cold-Roll reduction ratio (%) | SPM ratio (%) | Magnetic Shield (dB) | Electric Shield (dB) | Yield Strength (Kg/mm$^2$) | Configuration |
|---|---|---|---|---|---|---|
| Compar. 1 | 44 | 0 | 27.2 | 40.5 | 24.8 | Poor |
| 1 | 50 | 0 | 25.4 | 40.4 | 25.7 | Excellent |
| 2 | 67 | 0 | 25.2 | 40.1 | 26.2 | Excellent |
| Compar. 2 | 75 | 0 | 24.3 | 40.0 | 26.9 | Excellent |
| 3 | 50 | 0.2 | 25.2 | 40.2 | 25.5 | Excellent |
| 4 | 50 | 0.4 | 25.1 | 40.1 | 25.7 | Excellent |
| 5 | 67 | 0.3 | 25.0 | 40.0 | 26.3 | Excellent |
| Compar. 3 | 75 | 0.7 | 22.7 | 39.6 | 27.0 | Excellent |
| 6 | 44 | 0.5 | 25.6 | 40.3 | 25.0 | Excellent |
| Compar. 4 | 50 | 1.2 | 23.5 | 39.7 | 26.0 | Excellent |

As seen in Table 3, steel plates of the present invention (Steel Nos. Nos. 1 to 6), which ranged in cold-rolling reduction percentages from 44 to 70% with skin pass reduction percentage at 0.2~1.0%, were all excellent in electromagnetic shield effect with no deformation in configuration. Steel Nos. 1 and 2 in which the cold-rolling draft percentage was controlled within the range of 50~70% showed excellent electromagnetic and mechanical properties and excellent shape of steel plate even when skin pass was not conducted.

By contrast, from Comparative Steel No. 1 which was cold-rolled at a reduction percentage less than 50% and was not subjected to skin pass, distortion of plate defect was observed. When the cold-rolling reduction percentage was over 70% (Comparative Steel Nos. 2 and 3), the electromagnetic shield effect was drastically decreased.

At a skin pass reduction percentage of more than 1.0% (Comparative Steel No. 4), a large strain was introduced into the steel, giving rise to a decrease in permeability and conductivity under time-varying electromagnetic fields and thus in electromagnetic shield effect.

Controlling of contents of Cu and Sn, as described hereinbefore, is useful in manufacturing steel plates and hot-dip galvanized steel plates that show a yield strength of 22 kg/mm$^2$ or more and a shield efficiency of 93% or more (25 dB or higher) under time-varying electromagnetic fields at 60 Hz.

What is claimed is:

1. A high-strength steel plate with shield effect against time-varying electromagnetic field at low frequency and hot-dip galvanization property, prepared from a composition consisting essentially of C, N and S in an amount of 0.0150% by weight or less in total; Mn in an amount of 0.2 to 0.8% by weight; Al in an amount of 0.6% by weight or less; Si in an amount of 0.4% by weight or less; Cu and/or Sn in an amount of 0.1 to 0.6% by weight in total; Mn, Cu, Sn, Si and Al in a total amount of 1.0% by weight or less; the remainder of Fe and inevitably present elements; and
    said steel plate comprising a galvanized coating containing an anti-corrosive element thereon, said galvanized coating overlaid by a layer of far infrared radiation emitting powder which has a radiation efficiency of 0.9 with a thickness of 15–60 μm.

2. The high-strength steel plate as set forth in claim 1, wherein the steel plate has an electromagnetic shield effect of 25 dB or higher at 1 mm thickness and shows a yield strength of 22 kg/mm$^2$ or higher.

3. The steel plate as set forth in claim 1, further comprising an organic resin coating on the hot-dip galvanized coating.

4. The steel plate as set forth in claim 1, wherein the far infrared radiation emitting powder has a specific surface area of 1 m$^2$/g and comprises Mg(OH)$_2$ in an amount of 17–99% by weight.

* * * * *